US010987103B2

(12) United States Patent
Shelton, IV et al.

(10) Patent No.: US 10,987,103 B2
(45) Date of Patent: Apr. 27, 2021

(54) POWERED SURGICAL INSTRUMENT WITH LATCHING FEATURE PREVENTING REMOVAL OF BATTERY PACK

(71) Applicant: ETHICON LLC, Guaynabo, PR (US)

(72) Inventors: Frederick E. Shelton, IV, Hillsboro, OH (US); Kevin L. Houser, Springboro, OH (US); Michael J. Vendely, Lebanon, OH (US); Michael D. Auld, Blue Ash, OH (US); Brett E. Swensgard, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 326 days.

(21) Appl. No.: 15/634,475

(22) Filed: Jun. 27, 2017

(65) Prior Publication Data

US 2018/0368848 A1 Dec. 27, 2018

(51) Int. Cl.
*A61B 17/072* (2006.01)
*H01M 2/10* (2006.01)
(Continued)

(52) U.S. Cl.
CPC .. *A61B 17/07207* (2013.01); *A61B 17/00234* (2013.01); *A61B 17/072* (2013.01);
(Continued)

(58) Field of Classification Search
CPC ........ A61B 17/07207; A61B 17/00234; A61B 17/072; A61B 17/1155; A61B 2090/37; A61B 2090/0814; A61B 2017/00017; A61B 2017/0023; A61B 2017/0046; A61B 2017/00734; A61B 2090/037;
B25B 23/147; B25F 5/00; H01R 13/00; H01R 13/627; H01R 13/6278; H01R 13/41; H01R 13/42; H01R 13/415; H01R 13/422;
(Continued)

(56) References Cited

U.S. PATENT DOCUMENTS 6,783,524 B2 8/2004 Anderson et al.
7,000,818 B2 2/2006 Shelton, IV et al.
(Continued)

FOREIGN PATENT DOCUMENTS

| EP | 2 620 117 A1 | 7/2013 |
|---|---|---|
| EP | 3 065 201 A2 | 9/2016 |
| WO | WO 99/03186 A1 | 1/1999 |

OTHER PUBLICATIONS

U.S. Appl. No. 15/634,385, filed Jun. 27, 2017.
(Continued)

*Primary Examiner* — Dariush Seif
*Assistant Examiner* — Scott A Howell
(74) *Attorney, Agent, or Firm* — Frost Brown Todd LLC

(57) ABSTRACT

A surgical instrument includes a battery pack and a battery port. The battery pack includes a latching feature. The battery port is configured to receive the battery pack. The battery port includes a restraining feature. The restraining feature is configured to securely engage the latching feature when the battery port receives the battery pack such that the battery pack becomes fixedly attached to the battery port. At least a portion of the battery port is configured to permanently deform or break upon the removal of the battery pack from the battery port such that the surgical instrument becomes inoperable.

20 Claims, 11 Drawing Sheets

(51) Int. Cl.
*A61B 17/00* (2006.01)
*A61B 17/115* (2006.01)
*A61B 90/00* (2016.01)

(52) U.S. Cl.
CPC ......... *A61B 17/1155* (2013.01); *H01M 2/105* (2013.01); *A61B 2017/00017* (2013.01); *A61B 2017/0023* (2013.01); *A61B 2017/0046* (2013.01); *A61B 2017/00734* (2013.01); *A61B 2090/037* (2016.02); *A61B 2090/0814* (2016.02)

(58) Field of Classification Search
CPC ............ H01R 13/4223; H01R 13/4226; H01R 13/4285; H01R 13/432; H01R 13/4361; H01R 13/4362; H01R 13/4364; H01R 13/4365; H01R 13/4367; H01R 13/44; H01R 13/7036; H01R 13/707
USPC ......... 227/176.1; 29/730; 439/350–358, 761, 439/772, 818, 848; 218/16, 17, 19, 30
See application file for complete search history.

(56) References Cited

U.S. PATENT DOCUMENTS

| | | | |
|---|---|---|---|
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,959,050 B2* | 6/2011 | Smith | A61B 17/1155 227/175.2 |
| 8,408,439 B2 | 4/2013 | Huang et al. | |
| 8,453,914 B2 | 6/2013 | Laurent et al. | |
| 9,010,815 B2* | 4/2015 | Cooper | B25F 5/02 292/145 |
| 9,072,535 B2 | 7/2015 | Shelton, IV et al. | |
| 9,186,142 B2 | 11/2015 | Fanelli et al. | |
| 9,314,261 B2 | 4/2016 | Bales, Jr. et al. | |
| 9,692,036 B2 | 6/2017 | Bennett et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,843,134 B1* | 12/2017 | Mosholder | H01R 13/641 |
| 9,861,381 B2* | 1/2018 | Johnson | A61B 17/32009 |
| 2011/0017801 A1* | 1/2011 | Zemlok | A61B 17/07207 227/175.1 |
| 2011/0022032 A1 | 1/2011 | Zemlok et al. | |
| 2014/0263541 A1 | 9/2014 | Leimbach et al. | |
| 2015/0272575 A1 | 10/2015 | Leimbach et al. | |
| 2015/0272579 A1* | 10/2015 | Leimbach | A61L 2/087 227/178.1 |
| 2015/0280384 A1 | 10/2015 | Leimbach et al. | |
| 2016/0000305 A1* | 1/2016 | Elbaz | A61B 1/06 600/193 |
| 2017/0086823 A1 | 3/2017 | Leimbach et al. | |

OTHER PUBLICATIONS

U.S. Appl. No. 15/634,418, filed Jun. 27, 2017.
U.S. Appl. No. 15/634,436, filed Jun. 27, 2017.
U.S. Appl. No. 15/634,452, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,589, filed Jun. 27, 2017.
U.S. Appl. No. 15/634,620, filed Jun. 27, 2017.
European Search Report, Partial, and Written Opinion dated Sep. 12, 2018 for Application No. EP 18180191.1, 10 pgs.
International Search Report and Written Opinion dated Dec. 11, 2018 for Application No. PCT/IB2018/053661, 15 pgs.

* cited by examiner

POWERED SURGICAL INSTRUMENT WITH LATCHING FEATURE PREVENTING REMOVAL OF BATTERY PACK

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," Published Aug. 28, 2014, issued as U.S. Pat. No. 9,717,497 on Aug. 1, 2017; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
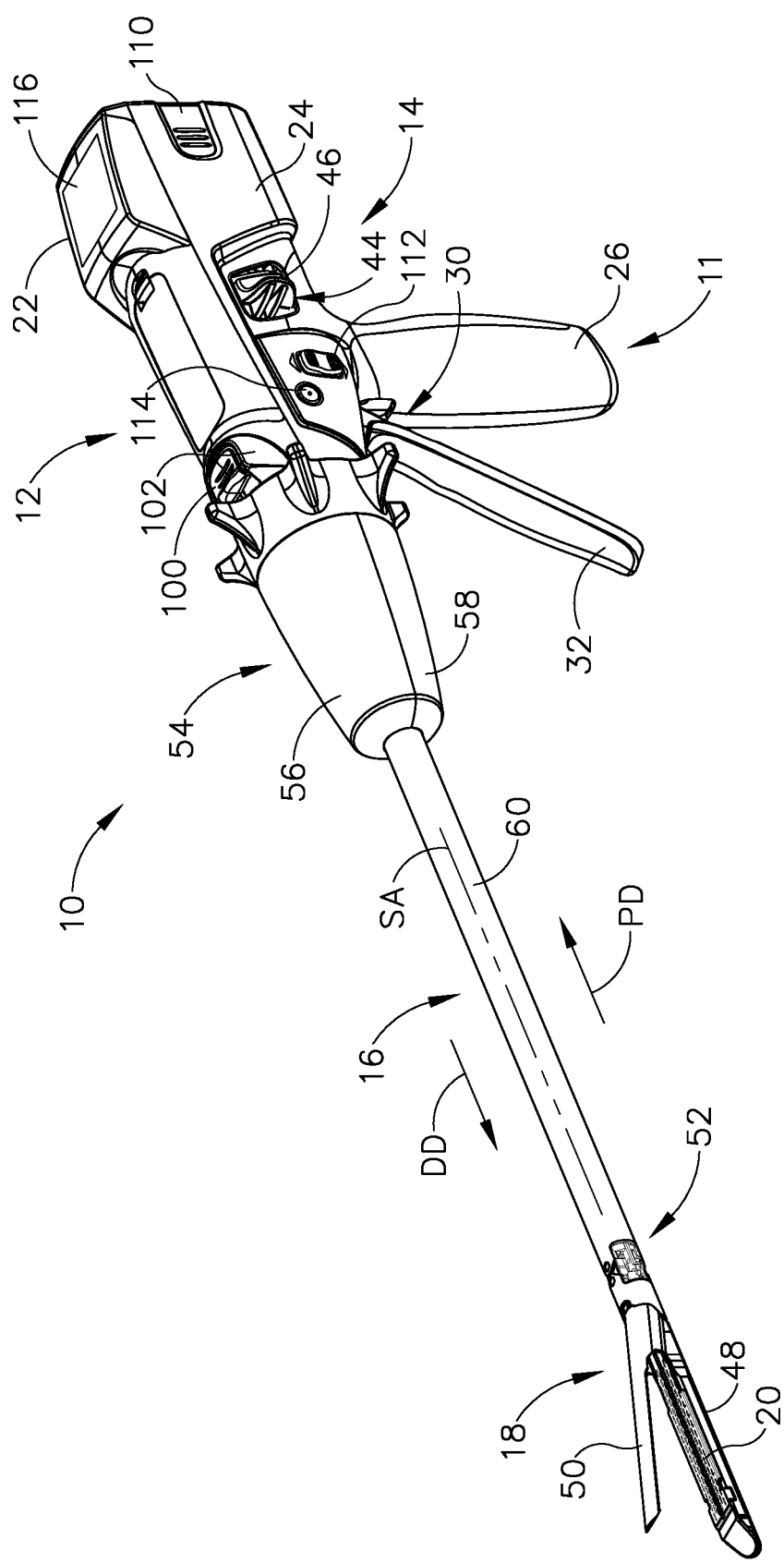
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
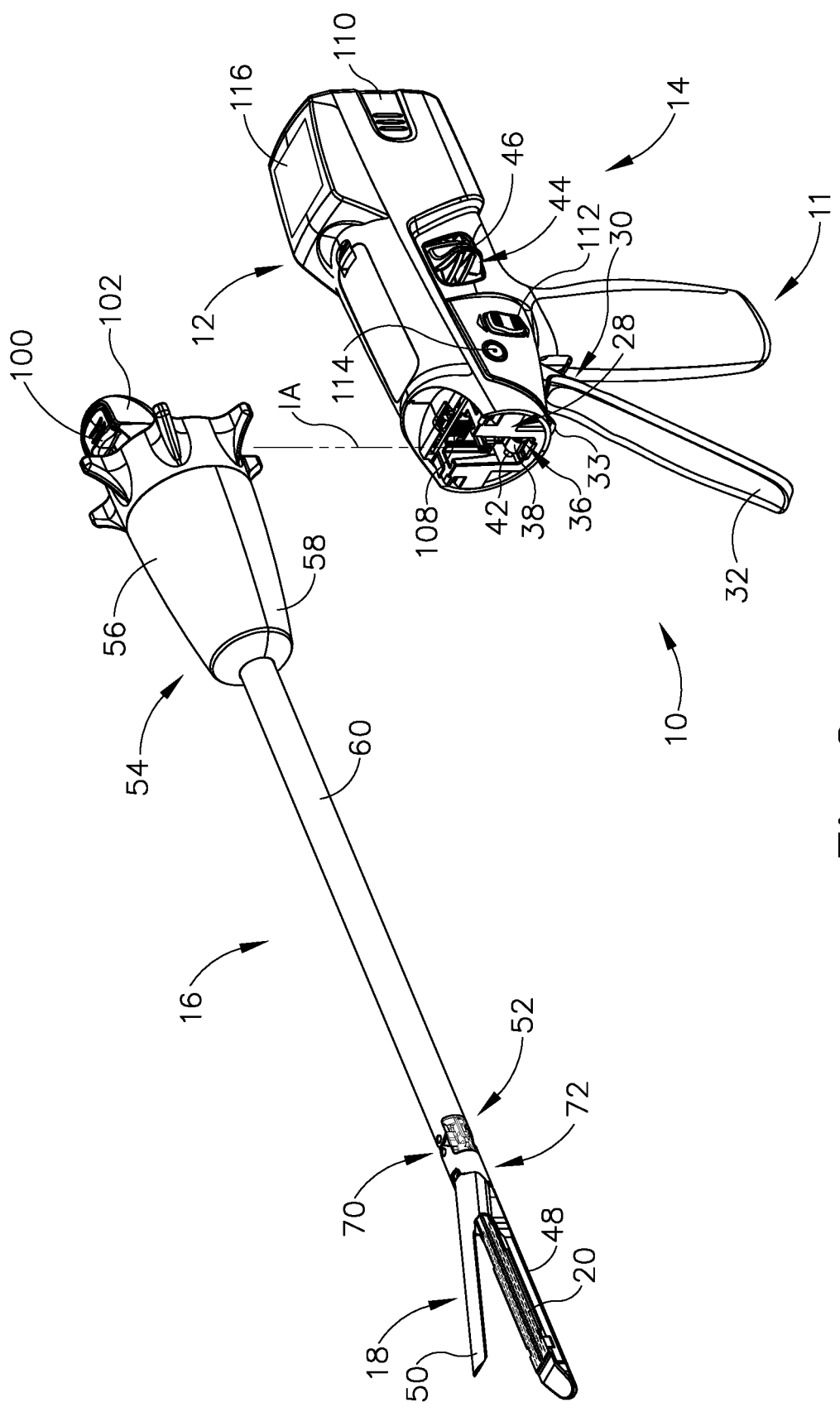
FIG. 2 depicts a perspective view of the instrument of FIG. 1, showing the shaft assembly disassembled from the handle assembly of the instrument.
Figure 3:
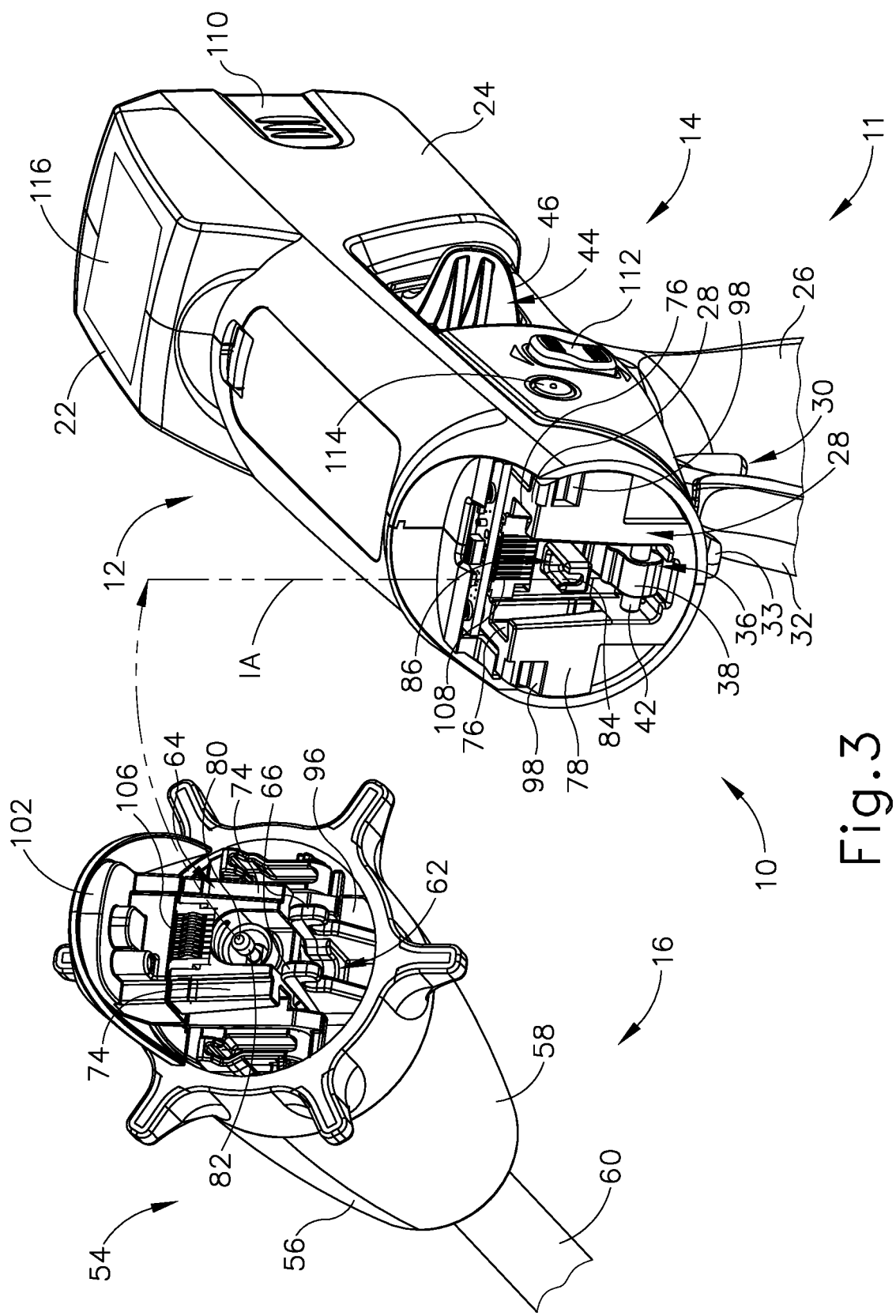
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
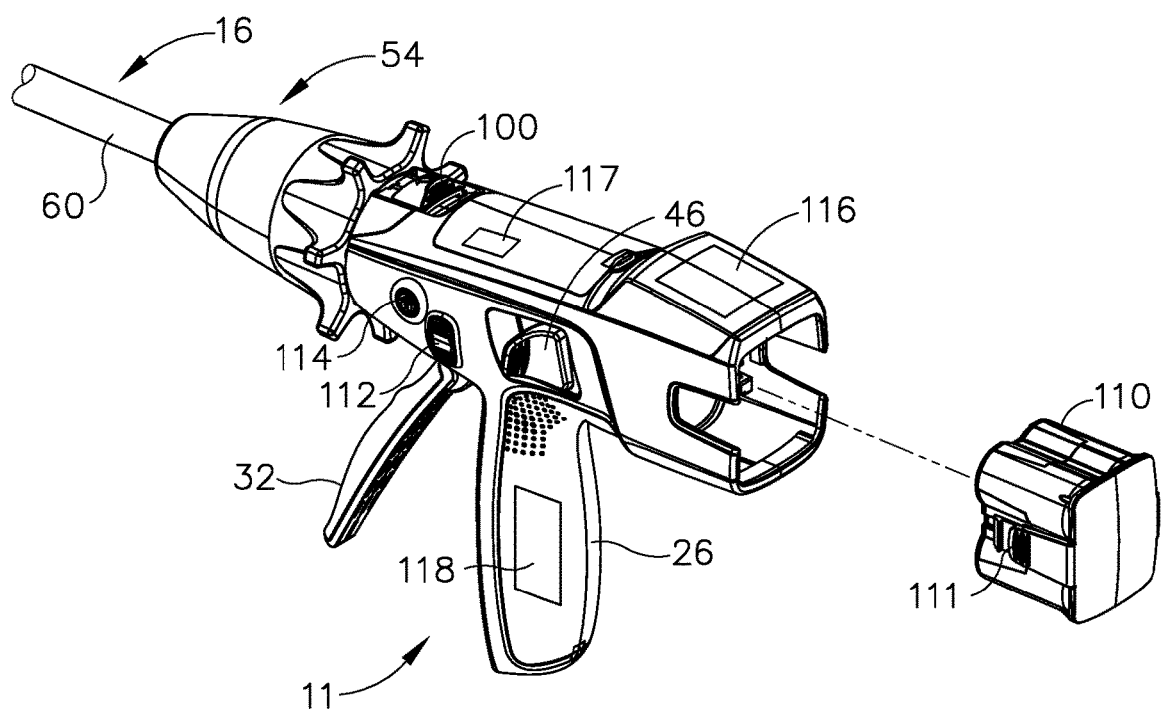
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) may be removed from handle (14) by exerting an inward force onto side buttons (111). In this instance, an operator may manipulate side buttons (111) inwardly to detach battery pack (110) from its secured engagement with handle (14). While pressing side buttons (111) inwardly, battery pack (110) may be proximally released from handle (14) thus allowing for the easy removal of battery pack (110) from surgical instrument (10). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, issued as U.S. Pat. No. 10,201,364 on Feb. 12, 2019, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, issued as U.S. Pat. No. 10,201,364 on Feb. 12, 2019, the disclosure of which is incorporated by reference herein; and/or in accordance with the teachings of various other references cited herein.

Figure 4A:
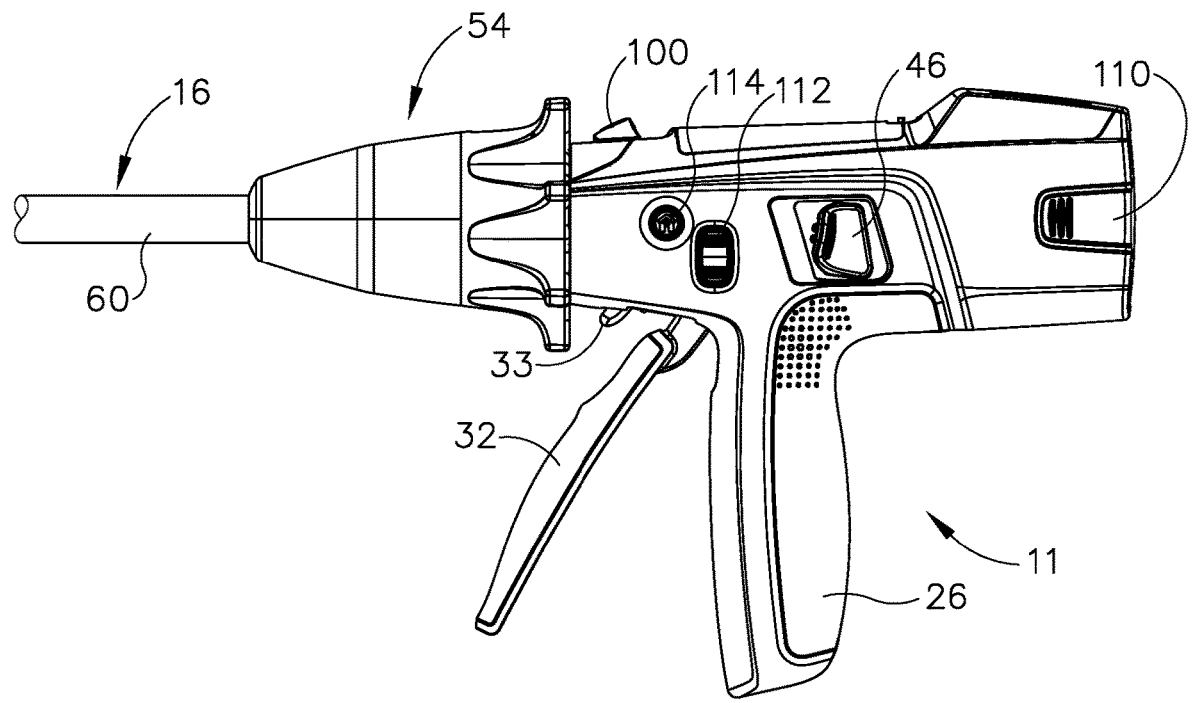
FIG. 4A depicts a side elevational view of a proximal portion of the instrument of FIG. 1, with a closure trigger in a first pivotal position and a firing trigger in a first pivotal position.
Figure 4B:
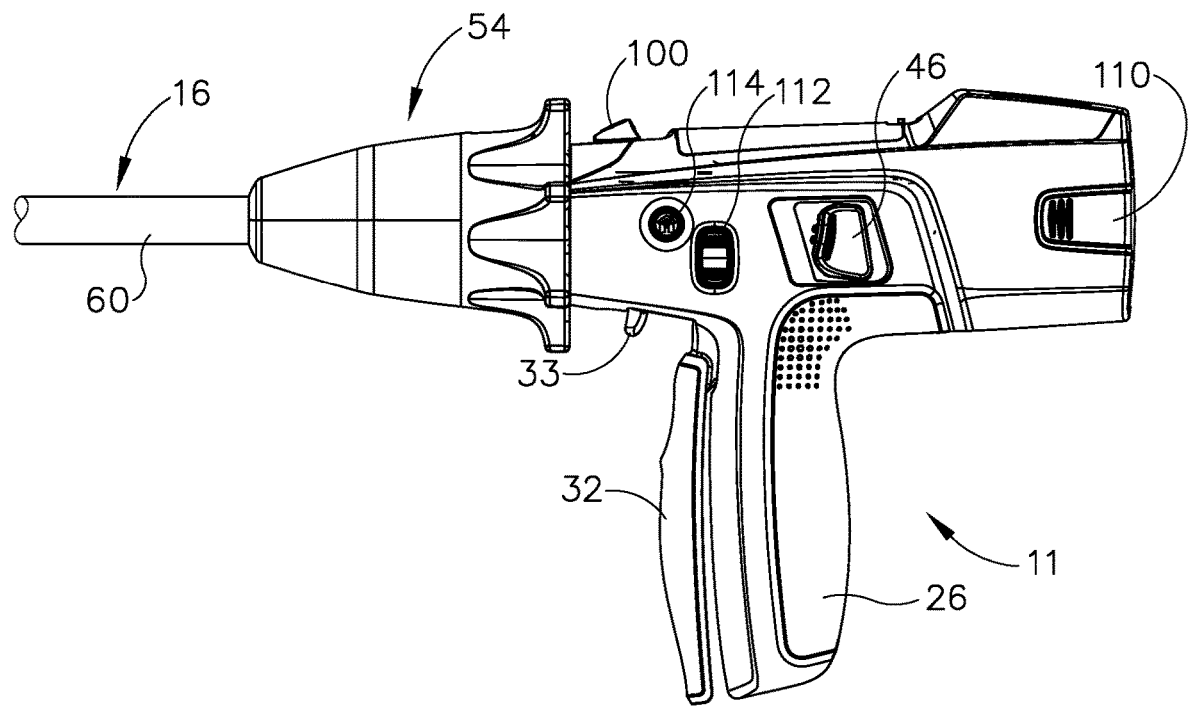
FIG. 4B depicts a side elevational view of a proximal portion of the instrument of FIG. 1, with the closure trigger in a second pivotal position and the firing trigger in a second pivotal position.
Figure 4C:
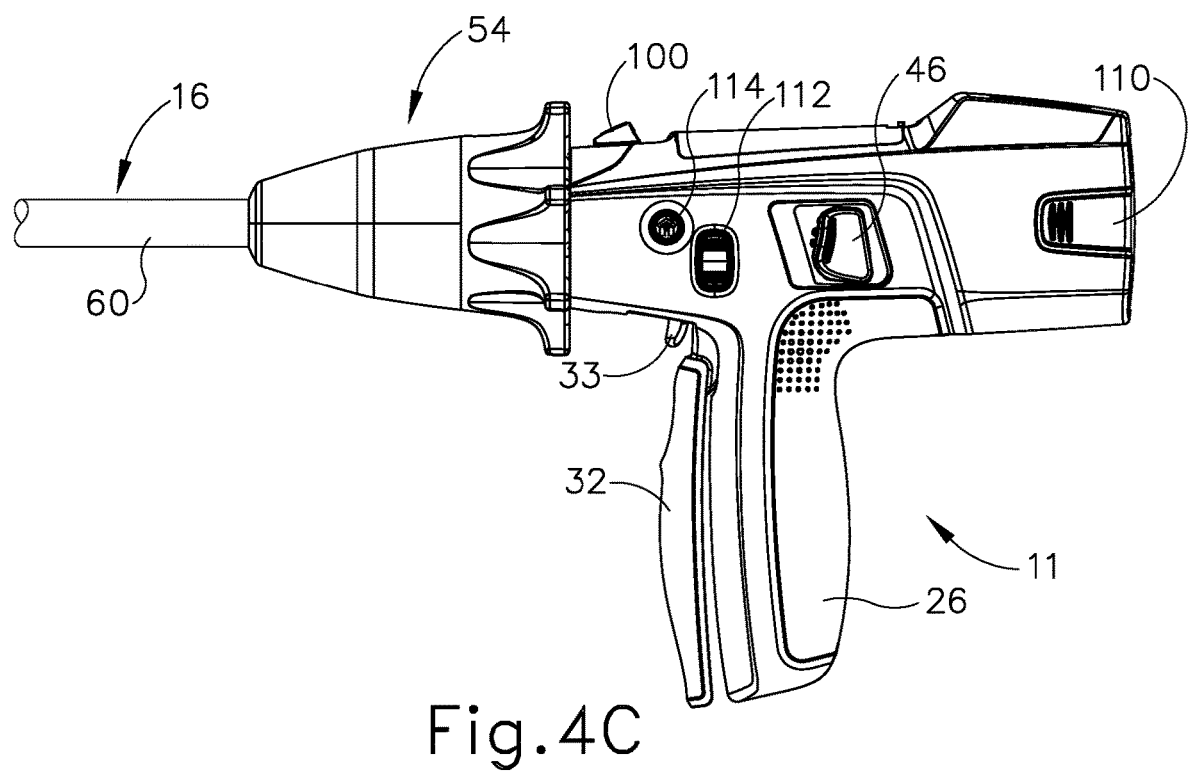
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, issued as U.S. Pat. No. 10,201,364 on Feb. 12, 2019, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364 on Feb. 12, 2019, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein and/or U.S. Pub. No. 2015/0272575, issued as U.S. Pat. No. 9,913,642 on Mar. 13, 2018, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
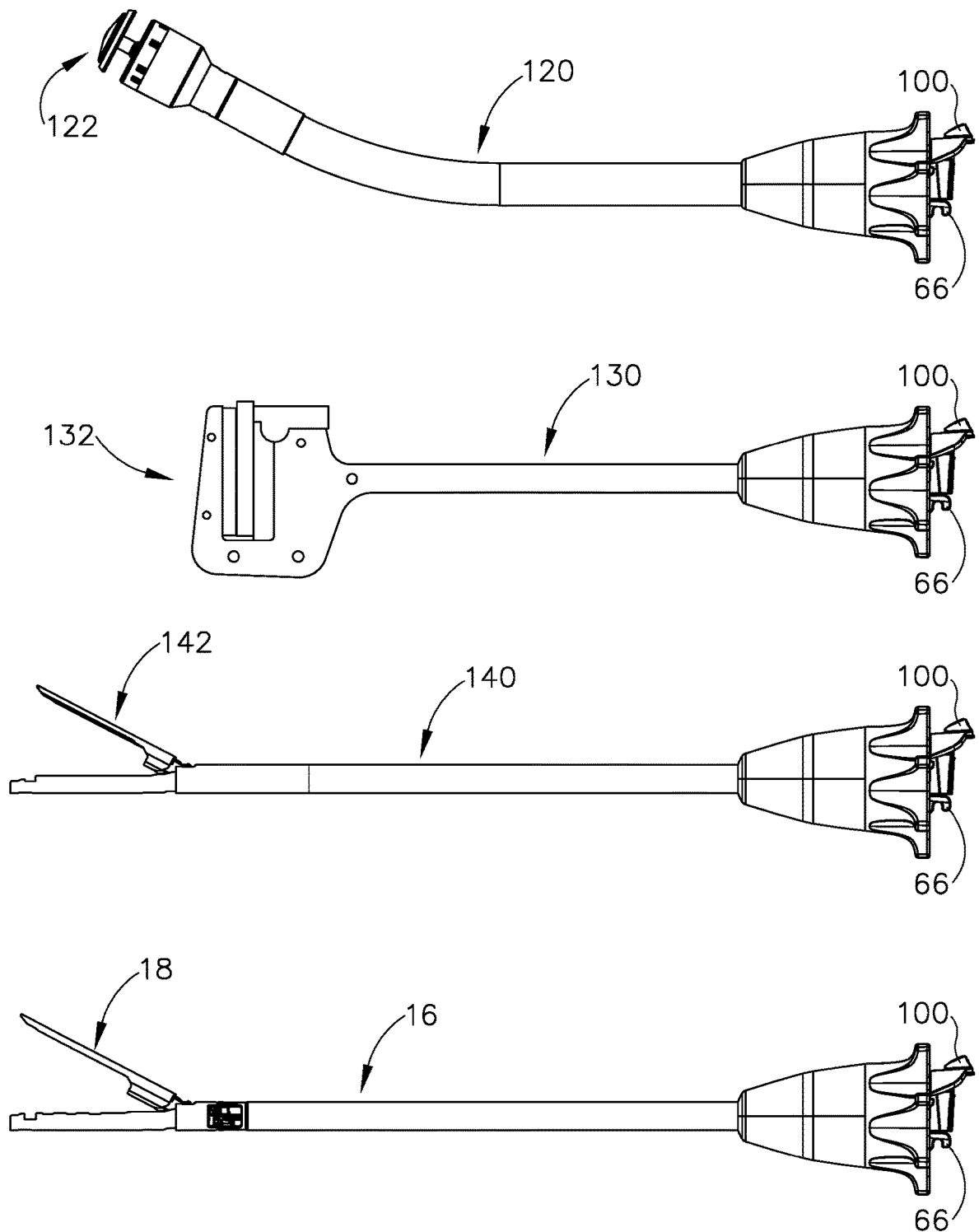
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, issued as U.S. Pat. No. 9,913,642 on Mar. 13, 2018, the disclosure of which is incorporated by reference herein. In addition or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. Exemplary Surgical Instrument and Battery Pack With Destructible Features

In some instances, it may be beneficial for a disposable, battery powered surgical instrument to be properly disposed when the ideal lifecycle of the surgical instrument has been exhausted. However, an operator may be tempted to improperly prolong the use of the surgical instrument beyond its ideal lifecycle despite the possible decline in performance of the surgical instrument and/or safeness of the surgical instrument after extensive use. A surgical instrument that structurally prevents further use of the instrument at the end of its expected lifecycle may be beneficial to prevent the continued overemployment of the surgical instrument.

In battery-powered instruments such as instrument (10) described above, it may be beneficial to initially provide battery (110) as a component that is separate from handle assembly (11), such that battery (110) is not inserted into handle assembly (11) until right before a surgical procedure is to begin. This practice may maximize the life of battery (110), minimizing the loss of power from battery (110)

before the surgical procedure. Nevertheless, battery (110) will eventually run out of charge, such that instrument (10) may no longer be fully operable when a dead battery (110) is coupled with handle assembly (11). This may tempt some operators to simply replace battery (110) with a fresh battery (110), thereby continuing use of instrument (10). However, it may be desirable from a safety and/or reliability standpoint to prevent instrument (10) from ever being used again after instrument (10) has been used long enough to fully discharge a battery (110). In other words, it may be desirable to limit the lifecycle of an entire instrument (10) to the life of a single battery (110), such that the lifecycle of an entire instrument (10) ends when the first battery (110) used in instrument (10) is fully discharged. It may further be desirable to enforce such a lifecycle by making it impossible (or at least highly impractical) to replace a discharged battery (110) and continue using instrument (10) thereafter.

The following description provides various examples of a battery powered surgical instrument and corresponding battery pack that are cooperatively configured to prevent the continued use of the surgical instrument beyond the lifecycle of the battery pack by effectively rendering the surgical instrument inoperable if the operator attempts to remove the battery pack. Ultimately, the destruction of the surgical instrument may be beneficial to ensure the surgical instrument is not overused beyond the lifespan of a single battery pack. It should be understood that the life cycle management features described below may be readily incorporated into in any of the various surgical instruments (10) and battery packs (110) described above and in any of the various surgical procedures described in the various references described herein. Other suitable ways in which the below-described surgical instruments and battery packs may be used will be apparent to those of ordinary skill in the art in view of the teachings herein.

A. Exemplary Surgical Instrument with Resilient Latching Features

Figure 7A:
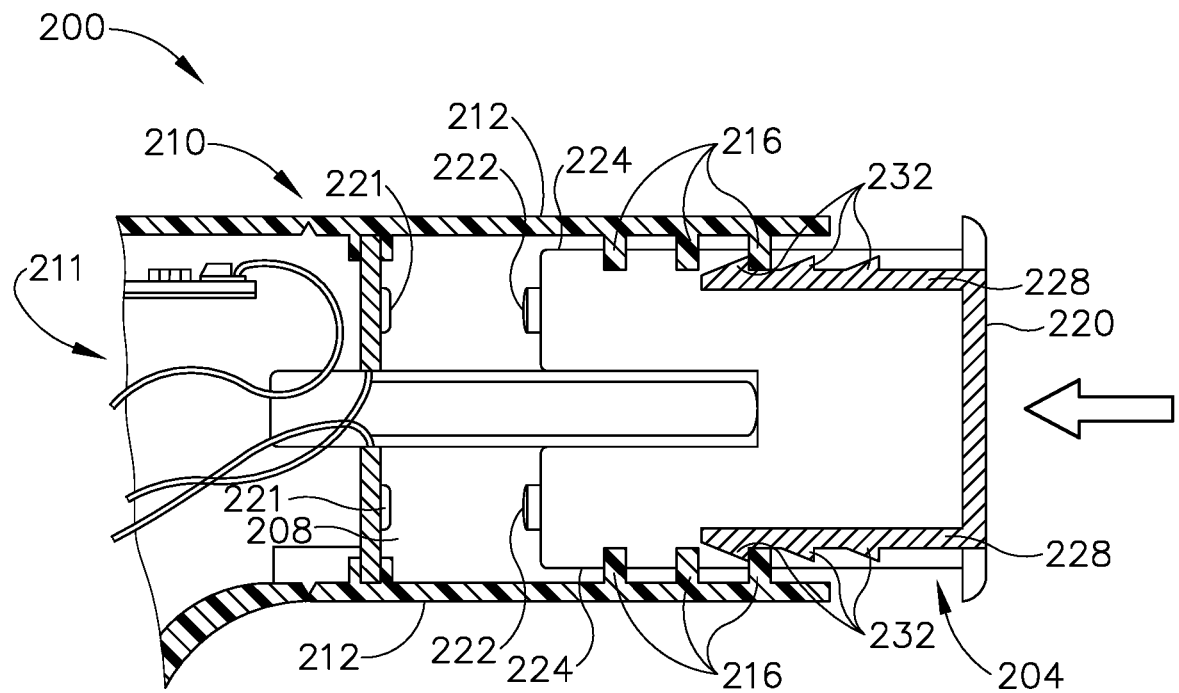
FIG. 7A depicts a cross sectional side view of an exemplary alternative battery pack being inserted into an exemplary variation of the surgical instrument of FIG. 1 and engaging latching features of the surgical instrument.

FIG. 7A shows an exemplary alternative handle assembly (211) comprising a battery receiving portion (210) and a battery pack (220). Except as otherwise described below, handle assembly (211) and battery pack (220) may be configured and operable just like handle assembly (11) and battery (110), respectively, described above. Battery receiving portion (210) includes an opening (204), a cavity (208), and inner walls (212) that are sized and configured to receive battery pack (220). Inner walls (212) of battery receiving portion (200) further include restraining features in the form of protrusions, specifically shown in the form of bosses (216) positioned along a longitudinal length of inner walls (212). Bosses (216) extend inwardly from inner wall (212) into cavity (208) and towards the opposing inner wall (212). As further seen in FIG. 7A, inner walls (212) may include multiple bosses (216) extending inwardly into cavity (212) of battery receiving portion (210). For exemplary purposes only, inner walls (212) may include three bosses (216), respectively. However, it will be apparent to those of ordinary skill in the art in view of the teachings herein that various quantities of bosses (216) may be suitable along inner walls (216). As with other components described herein, bosses (216) may be relocated, varied, modified, substituted, or supplemented in a variety of ways and configurations.

Battery pack (220) includes outer walls (224) and resilient arms (228) extending along a portion of outer walls (224). Outer walls (224) and arms (228) are sized and configured to be inserted into opening (204), cavity (208), and inner walls (212) of battery receiving portion (210). Battery pack (220) excludes the presence of any buttons and/or release features similar to side buttons (111) of battery pack (110) that are configured to allow for the removal of battery pack (220) from surgical instrument (200). Therefore, battery pack (220) is not configured to be easily disengaged from handle assembly (211) through the mere manipulation of a button or latch. In the present example, arms (228) of battery pack (220) further includes latching features in the form of protrusions, specifically shown in the form of catch elements (232) positioned along a longitudinal length of arms (228). Catch elements (232) extend outwardly from arms (228) and away from the opposing arm (228). It will be apparent to those of ordinary skill in the art that arms (228) may include multiple catch elements (232) in correspondence with the number of bosses (216) in battery receiving portion (200).

Bosses (216) of battery receiving portion (210) are sized and configured to engage catch elements (232) of battery pack (220) when battery pack (220) is inserted into battery receiving portion (210). Bosses (216) may be made from various materials that provide resilient deformation of arms (228), such that catch elements (232) ratchet along bosses (216) to thereby provide one-way inhibited movement of battery pack (220). Arms (228) are configured to bend inwardly towards the opposing arm (228) when catch elements (232) engage bosses (216). Arms (228) may be made from various materials that resiliently deflect while urging catch elements (232) into engagement with bosses (216). Catch elements (232) are made from a material similar to that of arms (228).

Figure 7B:
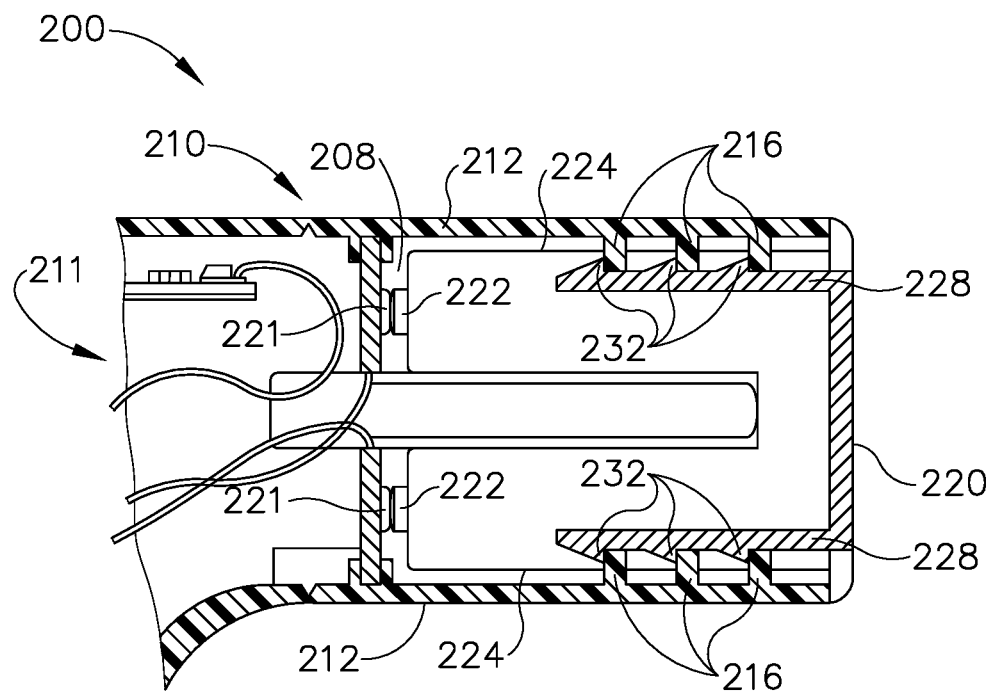
FIG. 7B depicts a cross sectional side view of the battery pack of FIG. 7A securely inserted into the surgical instrument of FIG. 7A and fully engaged by the latching features.

In the present example, bosses (216) serve to resiliently secure battery pack (220) to surgical instrument (200) when battery pack (220) is inserted into battery receiving portion (210). Bosses (216) may interlock with catch elements (232) as battery pack (220) is distally advanced into battery receiving portion (210) due to the lateral extension of bosses (216) into cavity (208), as seen in FIG. 7A. Once battery pack (220) is fully inserted distally into battery receiving portion (200), each boss (216) along each inner wall (212) is securely fixed against a corresponding catch element (232) positioned along arms (228), as seen in FIG. 7B. In this instance, catch elements (232) obstruct and inhibit the proximal extraction of battery pack (220) through the interlocking engagements with bosses (216). At the stage shown in FIG. 7B, electrical contacts (222) of battery pack (220) are engaged with complementary electrical contacts (221) of handle assembly (211), such that the instrument is ready for use in a surgical procedure.

Figure 7C:
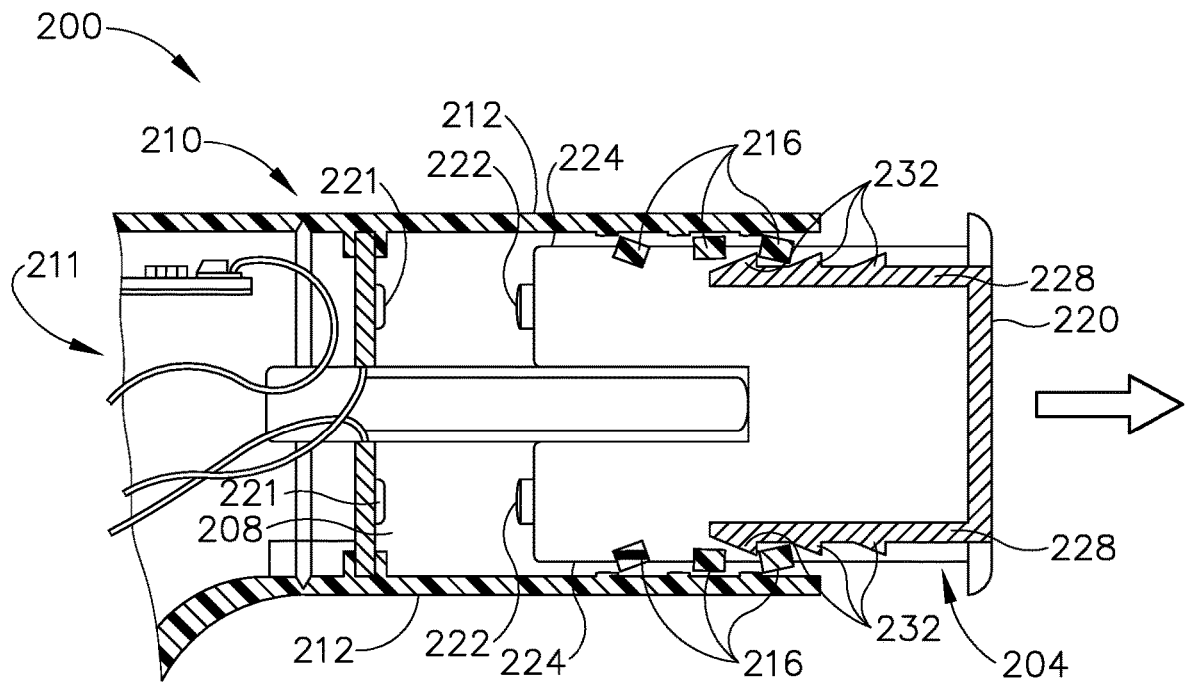
FIG. 7C depicts a cross sectional side view of the battery pack of FIG. 7A destructively removed from the surgical instrument of FIG. 7A and the latching features irreparably damaged.

At the end of a surgical procedure, the operator may attempt to remove battery pack (220) from handle assembly (211). In particular, the operator may wish to remove battery pack (220) to enable separate disposal of battery pack (220) and handle assembly (211). To remove battery pack (220) from handle assembly (211) a predetermined proximal force must be exerted by an operator to overcome the rigidity of bosses (216). As seen in FIG. 7C, applying the predetermined proximal force may ultimately overcome rigid strength of bosses (216), thus resulting in the forcible destruction of bosses (216). With bosses (216) destroyed, battery pack (220) may be completely removed from battery receiving portion (210). Once battery pack (220) has been completely removed from battery receiving portion (210), no subsequent battery pack (220) may be used with handle assembly (211) due to the permanent destruction of bosses (216). Thus, it may be ensured that surgical instrument (200) is not overused in excess of the lifespan of the original battery pack (220).

B. Exemplary Surgical Instrument With Weakened Neck Portion

Figure 8A:
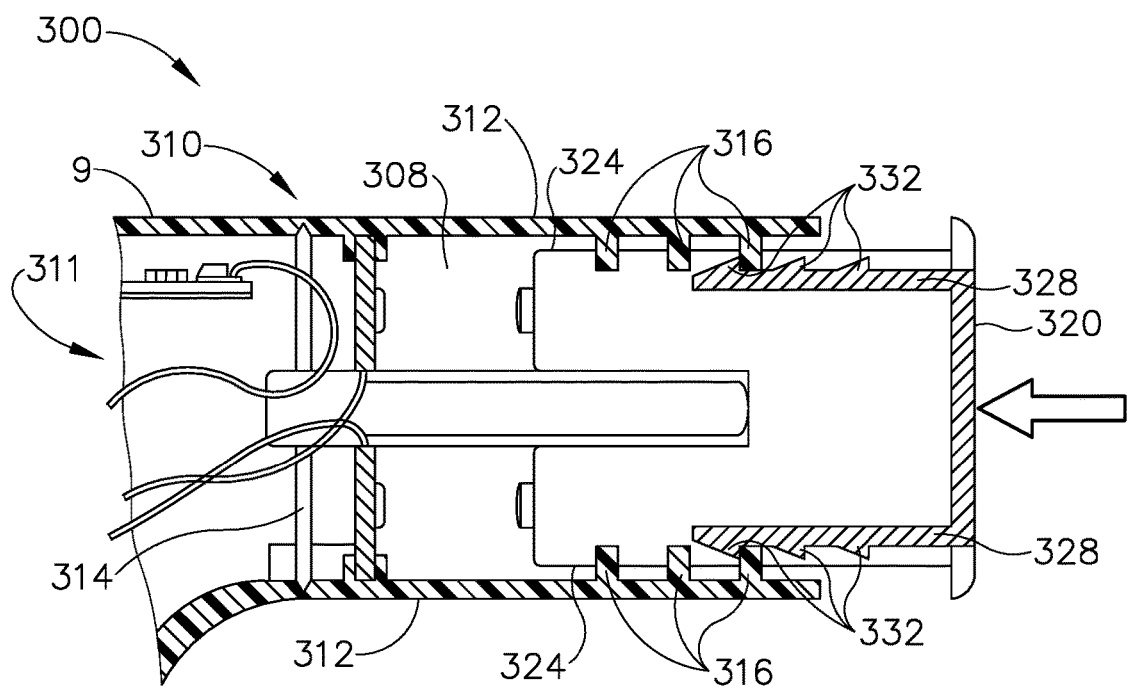
FIG. 8A depicts a cross sectional side view of another exemplary alternative battery pack being inserted into another exemplary variation of the surgical instrument of FIG. 1 and engaging latching features of the surgical instrument.

FIG. 8A illustrates an alternative exemplary surgical instrument (300) comprising a battery receiving portion (310) and a battery pack (320). Battery receiving portion (300) includes an opening (304), a cavity (308), and inner walls (312) that are sized and configured to receive battery pack (320). Battery receiving portion (300) further includes a weakened neck portion (314) positioned along a base (9) that serves to connect battery receiving portion (310) with the rest of handle assembly (311). Inner walls (312) of battery receiving portion (310) further include restraining features in the form of bosses (316) positioned along a longitudinal length of inner walls (312). Bosses (316) extend inwardly from inner wall (312) into cavity (308) and towards the opposing inner wall (312). As further seen in FIG. 8A, inner walls (312) may include multiple bosses (316) extending inwardly into cavity (308) of battery receiving portion (300). For exemplary purposes only, inner walls (312) may include three bosses (316), respectively. However, it will be apparent to those of ordinary skill in the art in view of the teachings herein that various quantities of bosses (316) may be suitable along inner walls (312). As with other components described herein, bosses (316) may be relocated, varied, modified, substituted, or supplemented in a variety of ways and configurations.

Weakened neck portion (314) is integrally and unitarily formed with battery receiving portion (310) and is configured to removably fix battery receiving portion (310) to handle assembly (311) up to a predetermined separating force. Weakened neck portion (314) is further configured fracture upon application of the predetermined separating force to thereby allow for the separation of battery receiving portion (310) from handle assembly (311).

Battery pack (320) includes outer walls (324) and resilient arms (328) extending along a portion of outer walls (324). Outer walls (324) and arms (328) are sized and configured to be inserted into opening (304), cavity (308), and inner walls (312) of battery receiving portion (310). Battery pack (320) excludes the presence of any buttons and/or release features similar to side buttons (111) of battery pack (110) and configured to allow for the removal of battery pack (320) from surgical instrument (300). Therefore, battery pack (320) is not configured to be easily disengaged from handle assembly (311) through the mere manipulation of a button or latch. In the present example, arms (328) of battery pack (320) further include latching features in the form of catch elements (332) positioned along a longitudinal length of arms (328). Catch elements (332) extend outwardly from arms (328) and away from the opposing arm (328). It will be apparent to those of ordinary skill in the art that arms (328) may include multiple catch elements (332) in correspondence with the number of bosses (316) in battery receiving portion (310).

Bosses (316) of battery receiving portion (310) are sized and configured to securely engage catch elements (332) of battery pack (320) when battery pack (320) is inserted into battery receiving portion (310). Bosses (316) may be made from various materials that provide deformation of catch elements (332) to thereby allow distal insertion of battery pack (320) into battery receiving portion (310); yet prevent proximal movement of battery pack (320) once battery pack (320) is inserted distally into battery receiving portion (310). Arms (328) are configured to bend inwardly towards the opposing arm (328) when catch elements (332) engage bosses (316). Arms (328) may be made from various materials that resiliently deflect while urging catch elements (332) into engagement with bosses (316). Catch elements (332) are made from a material similar to that of arms (328).

Figure 8B:
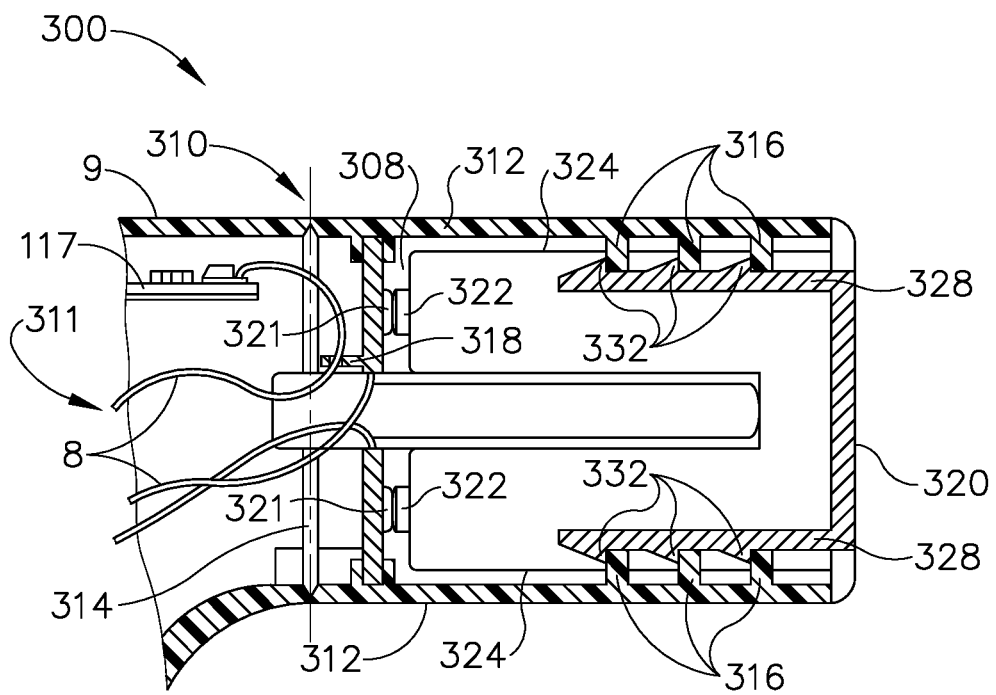
FIG. 8B depicts a cross sectional side view of the battery pack of FIG. 8A securely inserted into the surgical instrument of FIG. 8A and fully engaged by the latching features.

In the present example, bosses (316) serve to fixedly secure battery pack (320) to surgical instrument (300) when battery pack (320) is inserted into battery receiving portion (310). Bosses (316) may interlock with catch elements (332) as battery pack (320) is distally advanced into battery receiving portion (310) due to the lateral extension of bosses (316) into cavity (308), as seen in FIG. 8B. Once battery pack (320) is fully inserted distally into battery receiving portion (310), each fastener (316), along each inner wall (312), is securely fixed against a corresponding catch element (332) positioned along arms (328), as seen in FIG. 8B. In this instance, catch elements (332) obstruct and prevent the proximal extraction of battery pack (320) through the interlocking engagements with separating bosses (316). At the stage shown in FIG. 8B, electrical contacts (322) of battery pack (320) are engaged with complementary electrical contacts (321) of handle assembly (311), such that the instrument is ready for use in a surgical procedure.

Figure 8C:
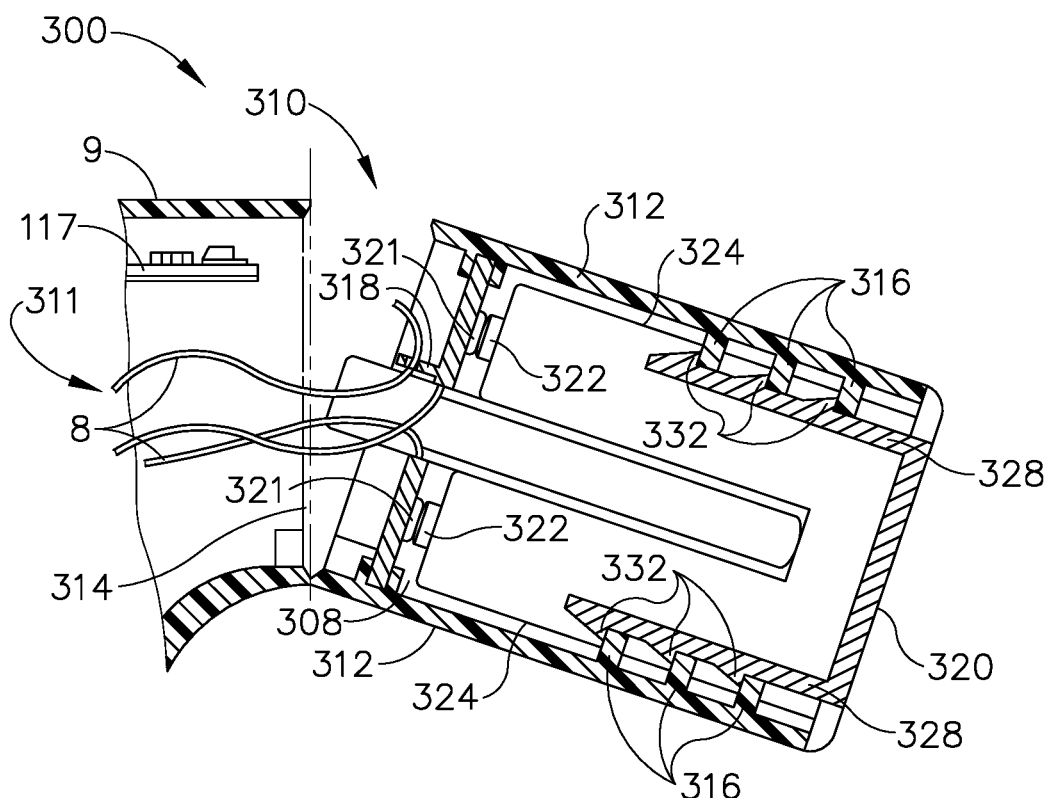
FIG. 8C depicts a cross sectional side view of the battery pack of FIG. 8A, with the portion of the surgical instrument of FIG. 8A holding the battery pack being destructively removed thereby irreparably damaging the surgical instrument.

At the end of a surgical procedure, the operator may attempt to remove battery pack (320) from surgical instrument (300). In particular, the operator may wish to remove battery pack (320) to enable separate disposal of battery pack (320) and handle assembly (311). To remove battery pack (320) from handle assembly (311), a predetermined proximal force must be exerted by an operator on battery pack (320). The application of proximal force on battery pack (320) may convey a stress on weakened neck portion (314) that may ultimately overcome the rigid strength of weakened neck portion (316). The interlocking engagement of bosses (316) and catch elements (332) are configured to withstand the application of the predetermined separating force upon battery receiving portion (310). As seen in FIG. 8C, applying the predetermined force on battery pack (320) may overcome the strength of weakened neck portion (314), causing neck portion (314) to fracture, thus resulting in the forcible destruction of battery receiving portion (310) along base (9). Once battery receiving portion (310) and battery pack (320) have together been completely detached from the rest of handle assembly (311), no subsequent battery pack (320) may be used with handle assembly (311) due to the permanent destruction of battery receiving portion (310). Thus, it may be ensured that surgical instrument (300) is not overused in excess of the lifespan of the original battery pack (320).

Battery receiving portion (310) may further include a shaft (301) and a bracket (318), as seen in FIG. 8B. Shaft (301) is configured to receive and hold battery pack (320) in cavity (308) of battery receiving portion (310). Bracket (318) is securely attached to shaft (301) and is configured to hold an electrical wire (8). Electrical wire (8) is electrically connected on one end of weakened neck portion (314) to control circuit (117) and on the other end of weakened neck portion (314) to battery pack (420). Prior to its connection with battery pack (320), electrical wire (8) is routed through and securely attached to bracket (318). Electrical wire (8) serves to provide electrical communication between battery pack (320), when inserted into battery receiving portion (310), and control circuit (117) of surgical instrument (300). Bracket (318) is configured to securely hold electrical wire (8) despite the application of the predetermined separating force upon battery receiving portion (310) along weakened neck portion (314).

As seen in FIG. 8C, applying the predetermined force may ultimately overcome the strength of neck portion (314), thus resulting in the forcible destruction of battery receiving portion (310) along base (9) and the permanent separation of electrical wire (8) from control circuit (117). Electrical wire (8) may be further separated at other positions between handle assembly (311) and battery receiving portion (310), such as from the engagement of electrical contacts (221, 222). Once battery receiving portion (310) has been completely detached from surgical instrument (300) no subsequent battery pack (320) may be used with surgical instrument (300) due to the permanent destruction of electrical wire (8) and thereby its electrical connection with control circuit (117) and electrical contacts (221, 222).

C. Exemplary Surgical Instrument With Adhesive Latching Feature

Figure 9:
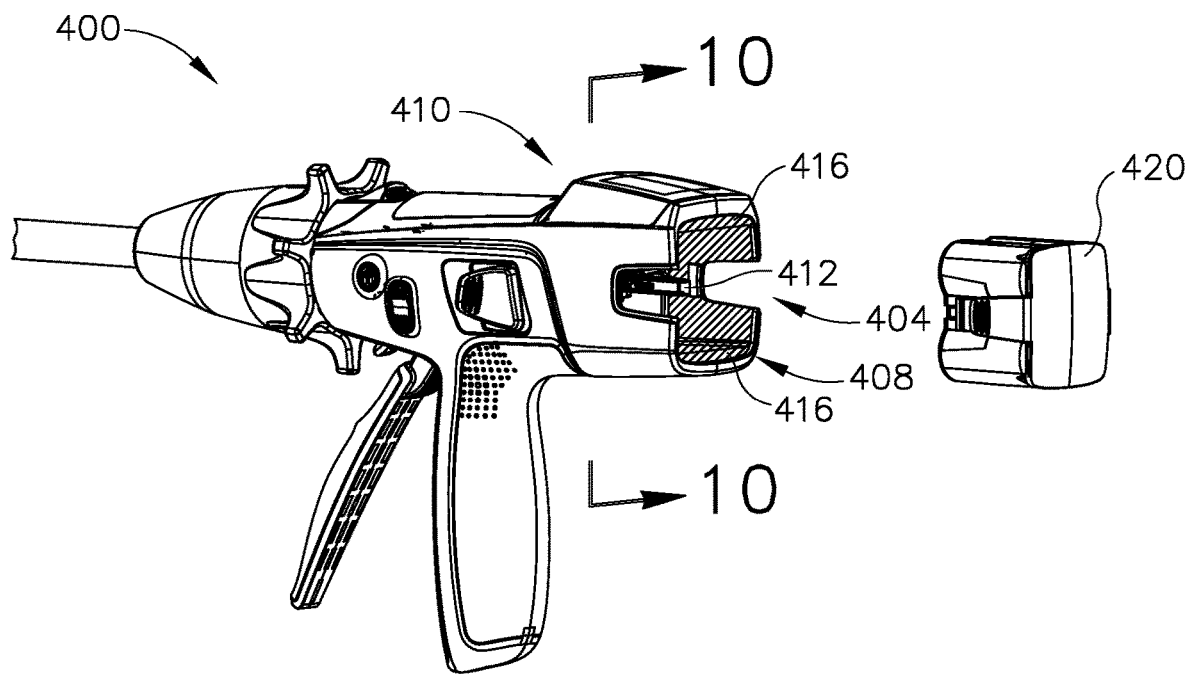
FIG. 9 depicts a perspective view of another exemplary surgical instrument, including a battery receiving portion with an adhesive material, with an exemplary alternative battery pack being inserted into the battery receiving portion.

FIG. 9 shows an exemplary alternative surgical instrument (400) comprising a battery receiving portion (410) and a battery pack (420). Except as otherwise described below, surgical instrument (400) of this example may be configured and operable just like surgical instrument (10) described above. Battery receiving portion (410) includes an opening (404) and a cavity (408) sized and configured to receive battery pack (420). Battery receiving portion (410) further includes a shaft (412) positioned in cavity (408). Shaft (412) extends proximally from surgical instrument (400) towards opening (404) and is configured to securely hold battery pack (420) in battery receiving portion (410). Battery receiving portion (410) further includes an adhesive material (416) configured to securely attach battery receiving portion (410) to any device or component inserted into opening (404), thereby securing the inserted component in battery receiving portion (410). Adhesive material (416) may be uniformly positioned along the inner surface of cavity (408) or the proximal edge defining opening (404). In addition, or in the alternative, adhesive material (416) may be positioned along the outer perimeter surface of shaft (412).

Adhesive material (416) may further serve to provide a sealed connection between battery pack (420) and battery receiving portion (410). As it will be understood by a person of ordinary skill in the art, it may be further beneficial to provide a sealing between battery pack (420) and battery receiving portion (410) since surgical instrument (400) may encounter various liquids during its ordinary use. For example, surgical instrument (400) may be subject to liquid exposures in an operating room, for instance the splashing of saline or the bodily fluids of a patient. By serving as a sealing component, adhesive material (416) may inhibit the invasion of any incidental bodily fluids or other substances from entering battery receiving portion (410) while surgical instrument (400) is in use. Adhesive material (416) may be an epoxy or any other suitable material that provides an adhesive, sealed connection between battery pack (420) and battery receiving portion (410).

Figure 10:
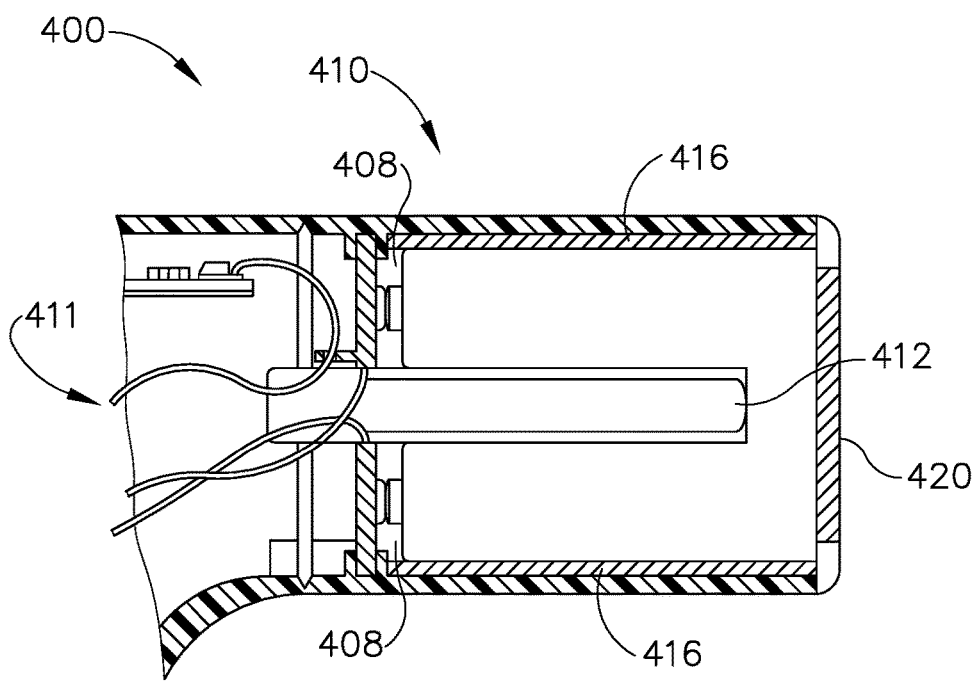
FIG. 10 depicts a cross sectional side view of the surgical instrument of FIG. 9, taken along line 10-10 of FIG. 9, with the battery pack of FIG. 9 fully inserted in the surgical instrument and adhesively secured to the battery receiving portion.

In the present example, as seen in FIG. 10, as battery pack (420) is inserted into battery receiving portion (410) the outer surface of battery pack (420) comes into contact with the internal surface of cavity (408) and the proximal edge defining opening (404). In this instance, battery pack (420) interacts with adhesive material (416) thereby resulting in the permanent attachment of battery receiving portion (410) and battery pack (420).

Adhesive material (416) is configured to withstand the application of a proximal force exerted by an operator on battery pack (420) to remove battery pack (420) from battery receiving portion (410). Therefore, battery pack (420) becomes permanently fixed to surgical instrument (400) thereby preventing any subsequent battery pack (420) from being used with surgical instrument (400).

D. Exemplary Battery Pack With Encrypted Destruction Code

Figure 11:
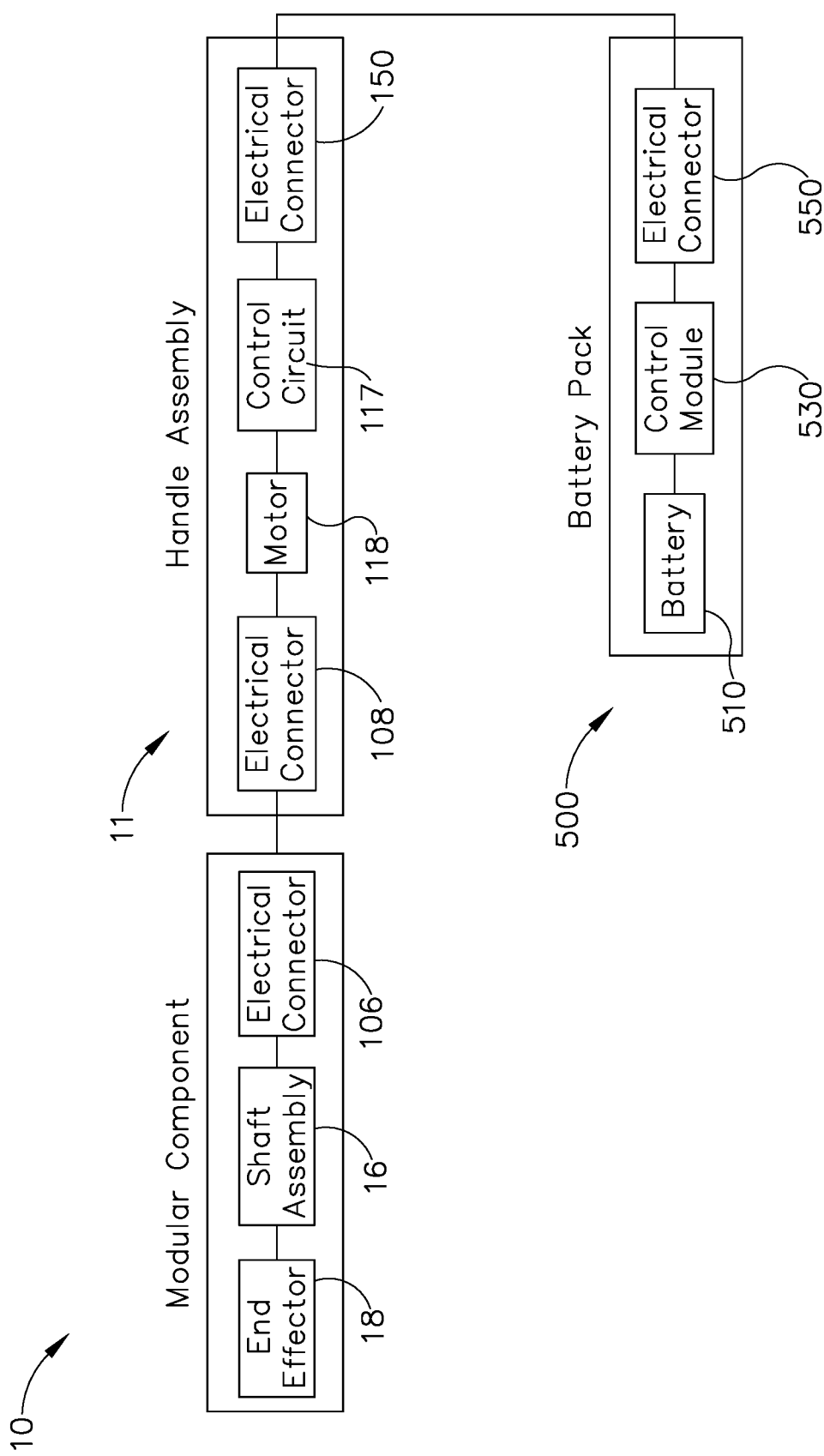
FIG. 11 presents a block schematic of an exemplary battery pack coupled with an exemplary variation of the surgical instrument of FIG. 1, the battery pack including a circuit board programmed to transmit a destruction code to the surgical instrument.

FIG. 11 presents a block schematic of an exemplary alternative battery pack (500) that may be used with a surgical instrument (10) described above. In the present example, battery pack (500) includes an electrical connector (550) that is operatively mounted to a control module (530). By way of example only, control module (530) may comprise various components as will be apparent to those of ordinary skill in the art in view of the teachings herein. Electrical connector (550) is configured for mating engagement with a corresponding electrical connector (150) on handle assembly (11) of surgical instrument (10). Battery pack (500) further includes a battery (510) electrically coupled to control module (530). Control module (530) is configured to store and execute algorithms to electrically transmit an encrypted destruction code from battery pack (500) to control circuit (117) of surgical instrument (10) when battery (510) gets near depletion.

In the present example, control module (530) is configured to actively monitor the electric charge of battery (510) to thereby determine when battery (510) is nearly depleted. In particular, control module (530) is configured to determine when the electric charge of battery (510) falls below a predetermined threshold value. The predetermined threshold value may be just above the amount of charge required to complete the processing steps described below. Upon identifying the near depleted state of battery (510), control module (530) transmits an electrical signal to control circuit (117) through electrical connectors (150, 550) communicating the encrypted destruction code. Control circuit (117) will then process the electrical signal and execute the destruction code to thereby render surgical instrument (10) inoperable from that point forward, thus necessitating its disposal. In some versions, the encrypted destruction code may contain electrical coding that serves to wipe the operational algorithms contained within control circuit (117). In some other versions, the encrypted destruction code may serve to create an interference for control circuit (117) from operating further. In still some other versions, the destruction code may serve to instruct control circuit (117) from ceasing all further operations. The encrypted destruction code is transmitted by control module (530) prior to initiating a final discharge mode of battery pack (500).

III. Exemplary Hydrophobic Coating for Medical Electronics

In some instances, it may be beneficial for the electrical connectors of a powered surgical instrument (10) commonly used in procedures having a risk of liquid ingress events to be protected from liquid exposure. As previously noted, surgical instruments (10) may be exposed to various liquids (e.g., blood, saline, etc.) during surgical procedures, and there may be risks associated with such liquids reaching electrical components (e.g., electrical connectors (106, 108, 150)) of instrument (10). Some conformal coatings may utilize acrylic or silicone chemistry and be applied on the surface of the electrical connector using a liquid spray or dip. However, coating electrical components (106, 108, 150) and conductors with a conformal coating may be problematic as they are non-conductive and thus create an insulating barrier that inhibits the components (106, 108, 150) from electrically functioning. Therefore, many circuit board (117) components that include conductive pads or contacts cannot be coated or else their electrical functionality will be negatively impacted. Applying a thin conductive coating on the electrical components (106, 108, 150) of a surgical instrument (10) may be beneficial to protect the contacts from potential liquid exposure while not hindering their electrical ability to function.

In particular, a thin coating of an exemplary conductive hydrophobic film may be applied to the connector contacts (106, 108, 150) of a surgical instrument (10) while not creating a mechanical barrier. By way of example only, the super-molecular ceramic coating Repellix™ created by Integrated Surface Technologies, Inc., of Menlo Park, Calif., may be a suitable version of the conductive hydrophobic film described above. Alternatively, Penetrox™ created by Burndy, LLC, of Manchester, N.H., may be another suitable version of the conductive hydrophobic film. By not creating a mechanical barrier, the conductive hydrophobic coating allows the connector contacts (106, 108, 150), which rely on pressure interface to create an electrical connection, to function properly. While a typical coating process of circuit boards (117) may require the additional cost and labor effort to mask any connectors or contact pads from being covered by the conformal coating, the conductive hydrophobic coating may be applied uniformly across the circuit board (117) thus improving manufacturing efficiency and reducing costs.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) a battery pack, wherein the battery pack includes a latching feature; (b) a battery port, wherein the battery port is configured to receive the battery pack, wherein the battery port includes a restraining feature; wherein the restraining feature is configured to securely engage the latching feature when the battery port receives the battery pack such that the battery pack becomes fixedly attached to the battery port; and wherein at least a portion of the battery port is configured to permanently deform or break upon the removal of the battery pack from the battery port such that the surgical instrument becomes inoperable.

EXAMPLE 2

The surgical instrument of Example 1, wherein the restraining feature comprises a protrusion, wherein the latching feature comprises a catch.

EXAMPLE 3

The surgical instrument of Example 2, wherein the battery pack includes multiple catches, wherein the battery port includes multiple protrusions comparative to the multiple catches.

EXAMPLE 4

The surgical instrument of Example 3, wherein the battery port includes a first and second internal wall, wherein the multiple protrusions extend into the battery port from the first and second internal walls.

EXAMPLE 5

The surgical instrument of Example 4, wherein the multiple catches are configured to permanently deform the multiple protrusions when the battery pack is removed from the battery port.

EXAMPLE 6

The surgical instrument of any one or more of Examples 1 through 5, wherein the battery port further comprises a weakened portion, wherein the weakened portion is integral with the battery port, wherein the weakened portion is positioned along a base of the battery port.

EXAMPLE 7

The surgical instrument of Example 6, wherein the weakened portion is configured to permanently deform upon removal of the battery pack from the battery port such that the battery pack and the battery port are jointly detached from the surgical instrument at the weakened portion and along the base.

EXAMPLE 8

The surgical instrument of Example 7, wherein the battery port further includes at least one electrical wire, wherein the at least one electrical wire is operable to electrically connect the battery pack to a circuit board of the surgical instrument.

EXAMPLE 9

The surgical instrument of Example 8, wherein the battery port further includes a restrictive bracket, wherein the restrictive bracket is configured to securely grasp the at least one electrical wire.

EXAMPLE 10

The surgical instrument of Example 9, wherein the restrictive bracket is operable to permanently detach the at least one electrical wire from one or both of the circuit board or the battery pack when the weakened portion permanently deforms such that the battery pack is electrically disconnected from the circuit board.

EXAMPLE 11

The surgical instrument of any one or more of Examples 1 through 10, wherein the restraining feature comprises an adhesive material positioned within the battery port.

EXAMPLE 12

The surgical instrument of Example 11, wherein the latching feature comprises a proximal receiving edge of the battery port.

EXAMPLE 13

The surgical instrument of Example 12, wherein the adhesive material is configured to permanently attach the battery pack to the battery port when the battery pack is inserted into the battery port and contacts the proximal receiving edge.

EXAMPLE 14

The surgical instrument of any one or more of Examples 11 through 13, wherein the latching feature comprises an inner surface of the battery port.

EXAMPLE 15

The surgical instrument of Example 14, wherein the adhesive material is configured to permanently attach the battery pack to the battery port when the battery pack is inserted into the battery port and contacts the inner surface of the battery port.

EXAMPLE 16

A surgical instrument, comprising: (a) a battery, wherein the battery includes a fastener; (b) a port, wherein the port is configured to receive the battery, wherein the port includes a latch element configured to mate with the fastener when the port receives the battery; and wherein the battery is configured to irreparably destruct the port or latch element when removed from the port such that the battery may not be removed from the port without damaging the port or latch element.

EXAMPLE 17

The surgical instrument of Example 16, wherein the fastener comprises at least one catch, wherein the latch element comprises at least one protrusion, wherein the at least one catch is configured to permanently deform the at least one protrusion when the battery is removed from the port.

EXAMPLE 18

The surgical instrument of any one or more of Examples 16 through 17, wherein the port includes a perforated neck, wherein the mating engagement of the fastener and latch element is operable to permanently deform the perforated neck when the battery is removed from the port.

EXAMPLE 19

The surgical instrument of any one or more of Examples 16 through 18, wherein the fastener comprises an adhesive, wherein the latch element comprises a lumen configured to link the battery to the port, wherein the adhesive is operable to fixedly attach the battery to the port such that the port is permanently deformed when the battery is removed.

EXAMPLE 20

A method of transmitting an encrypted destruction code from a battery pack to a surgical instrument upon the near depletion of the battery pack, the method comprising: (a) providing the surgical instrument with power from the battery pack until the remaining charge in the battery pack falls below a predetermined threshold; (b) transmitting an encrypted code from a control module of the battery pack to a control circuit of the surgical instrument when the remaining charge in the battery pack falls below the predetermined threshold; (c) receiving the encrypted code at the control circuit and unencrypting the code; and (d) processing the unencrypted code and thereby rendering the surgical instrument inoperable for continued use.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent Ser. No. 15/634,385, entitled "Apparatus and Method to Determine End of Life of Battery Powered Surgical Instrument," filed on Jun. 27, 2017, issued as U.S. Pat. No. 10,835,218 on Nov. 17, 2020, the disclosure of which is incorporated by reference herein. Various suitable ways in which the teachings herein may be combined with the teachings of U.S. patent Ser. No. 15/634,385, issued as U.S. Pat. No. 10,835,218 on Nov. 17, 2020, will be apparent to those of ordinary skill in the art in view of the teachings herein.

In addition to the foregoing, the teachings herein may be readily combined with the teachings of U.S. patent Ser. No. 15/634,418, entitled "Surgical Instrument with Integrated and Independently Powered Displays," filed on Jun. 27, 2017, issued as U.S. Pat. No. 10,163,309 on Dec. 25, 2018, the disclosure of which is incorporated by reference herein. Various suitable ways in which the teachings herein may be combined with the teachings of U.S. patent Ser. No. 15/634,418, issued as U.S. Pat. No. 10,163,309 on Dec. 25, 2018, will be apparent to those of ordinary skill in the art in view of the teachings herein.

In addition to the foregoing, the teachings herein may be readily combined with the teachings of U.S. patent Ser. No. 15/634,436, entitled "Battery Pack with Integrated Circuit Providing Sleep Mode to Battery Pack and Associated Surgical Instrument," filed on Jun. 27, 2017, issued as U.S. Pat. No. 10,639,018 on May 5, 2020, the disclosure of which is incorporated by reference herein. Various suitable ways in which the teachings herein may be combined with the teachings of U.S. patent Ser. No. 15/634,436, issued as U.S. Pat. No. 10,639,018 on May 5, 2020, will be apparent to those of ordinary skill in the art in view of the teachings herein.

In addition to the foregoing, the teachings herein may be readily combined with the teachings of U.S. patent Ser. No. 15/634,452, entitled "Battery Powered Surgical Instrument with Dual Power Utilization Circuits for Dual Modes," filed on Jun. 27, 2017, the disclosure of which is incorporated by reference herein. Various suitable ways in which the teachings herein may be combined with the teachings of U.S.

patent Ser. No. 15/634,452, issued as U.S. Pat. No. 10,511,065 on Dec. 17, 2019, will be apparent to those of ordinary skill in the art in view of the teachings herein.

In addition to the foregoing, the teachings herein may be readily combined with the teachings of U.S. patent Ser. No. 15/634,497, entitled "Modular Powered Electrical Connection for Surgical Instrument with Features to Prevent Electrical Discharge" filed on Jun. 27, 2017, issued as U.S. Pat. No. 10,667,812 on Jun. 2, 2020, the disclosure of which is incorporated by reference herein. Various suitable ways in which the teachings herein may be combined with the teachings of U.S. patent Ser. No. 15/634,497, issued as U.S. Pat. No. 10,667,812 on Jun. 2, 2020, will be apparent to those of ordinary skill in the art in view of the teachings herein.

In addition to the foregoing, the teachings herein may be readily combined with the teachings of U.S. patent Ser. No. 15/634,524, entitled "Powered Surgical Instrument with Independent Selectively Applied Rotary and Linear Drivetrains," filed on Jun. 27, 2017, issued as U.S. Pat. No. 10,888,324 on Jan. 12, 2021, the disclosure of which is incorporated by reference herein. Various suitable ways in which the teachings herein may be combined with the teachings of U.S. patent Ser. No. 15/634,524, issued as U.S. Pat. No. 10,888,324 on Jan. 12, 2021, will be apparent to those of ordinary skill in the art in view of the teachings herein.

In addition to the foregoing, the teachings herein may be readily combined with the teachings of U.S. patent Ser. No. 15/634,556, entitled "Powered Circular Stapler with Reciprocating Drive Member to Provide Independent Stapling and Cutting of Tissue," filed on Jun. 27, 2017, published as U.S. Pub. No. 2018/0368851 on Dec. 27, 2018, the disclosure of which is incorporated by reference herein. Various suitable ways in which the teachings herein may be combined with the teachings of U.S. patent Ser. No. 15/634,556, published as U.S. Pub. No. 2018/0368851 on Dec. 27, 2018will be apparent to those of ordinary skill in the art in view of the teachings herein.

In addition to the foregoing, the teachings herein may be readily combined with the teachings of U.S. patent Ser. No. 15/634,620, entitled "Surgical Stapler with Independently Actuated Drivers to Provide Varying Staple Heights," filed on Jun. 27, 2017, issued as U.S. Pat. No. 10,828,029 on Nov. 10, 2020, the disclosure of which is incorporated by reference herein. Various suitable ways in which the teachings herein may be combined with the teachings of U.S. patent Ser. No. 15/634,620, issued as U.S. Pat. No. 10,828,029 on Nov. 10, 2020, will be apparent to those of ordinary skill in the art in view of the teachings herein.

In addition to the foregoing, the teachings herein may be readily combined with the teachings of U.S. patent Ser. No. 15/634,589, entitled "Surgical Instrument Handle Assembly with Feature to Clean Electrical Contacts at Modular Shaft Interface," filed on Jun. 27, 2017, issued as U.S. Pat. No. 10,090,616 on Oct. 2, 2018, the disclosure of which is incorporated by reference herein. Various suitable ways in which the teachings herein may be combined with the teachings of U.S. patent Ser. No. 15/634,589, issued as U.S. Pat. No. 10,090,616 on Oct. 2, 2018, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector operable to treat tissue, wherein the end effector includes:
      (i) a first member, and
      (ii) a second member selectively actuatable relative to the first member to clamp tissue therebetween;
   (b) a shaft assembly extending proximally from the end effector;
   (c) a handle assembly coupled with a proximal end of the shaft assembly,
      wherein the handle assembly includes:
      (i) a motor operable to actuate the end effector, and
      (ii) a battery port, wherein the battery port includes a port interior and a restraining feature arranged within the port interior; and
   (d) a battery pack configured to be inserted into the battery port and power the motor, wherein the battery pack includes a latching feature,
   wherein the restraining feature is configured to securely engage the latching feature within the port interior when the battery port receives the battery pack such that the battery pack becomes fixedly attached to the battery port; and
   wherein at least a portion of the battery port is configured to permanently deform or break upon removal of the battery pack from the battery port such that the surgical instrument becomes inoperable.

2. The surgical instrument of claim 1, wherein the restraining feature comprises a protrusion, wherein the latching feature comprises a catch.

3. The surgical instrument of claim 2, wherein the battery pack includes multiple catches, wherein the battery port includes multiple protrusions comparative to the multiple catches.

4. The surgical instrument of claim 3, wherein the battery port includes a first and second internal wall, wherein the multiple protrusions extend into the battery port from the first and second internal walls.

5. The surgical instrument of claim 4, wherein the multiple catches are configured to permanently deform the multiple protrusions when the battery pack is removed from the battery port.

6. The surgical instrument of claim 1, wherein the battery port further comprises a weakened portion, wherein the weakened portion is integral with the battery port, wherein the weakened portion is positioned along a base of the battery port.

7. The surgical instrument of claim 6, wherein the weakened portion is configured to permanently deform upon removal of the battery pack from the battery port such that the battery pack and the battery port are jointly detached from the surgical instrument at the weakened portion and along the base.

8. The surgical instrument of claim 7, wherein the battery port further includes at least one electrical wire, wherein the at least one electrical wire is operable to electrically connect the battery pack to a circuit board of the surgical instrument.

9. The surgical instrument of claim 8, wherein the battery port further includes a restrictive bracket, wherein the restrictive bracket is configured to securely grasp the at least one electrical wire.

10. The surgical instrument of claim 9, wherein the restrictive bracket is operable to permanently detach the at least one electrical wire from one or both of the circuit board or the battery pack when the weakened portion permanently deforms such that the battery pack is electrically disconnected from the circuit board.

11. The surgical instrument of claim 1, wherein the restraining feature comprises an adhesive material positioned within the battery port.

12. The surgical instrument of claim 11, wherein the latching feature comprises a proximal receiving edge of the battery port.

13. The surgical instrument of claim 12, wherein the adhesive material is configured to permanently attach the battery pack to the battery port when the battery pack is inserted into the battery port and contacts the proximal receiving edge.

14. The surgical instrument of claim 11, wherein the latching feature comprises an inner surface of the battery port.

15. The surgical instrument of claim 14, wherein the adhesive material is configured to permanently attach the battery pack to the battery port when the battery pack is inserted into the battery port and contacts the inner surface of the battery port.

16. The surgical instrument of claim 1, wherein the end effector is operable to staple tissue when actuated by the motor in response to the motor being powered by the battery pack.

17. The surgical instrument of claim 1, wherein the battery port opens proximally at a proximal end of the handle assembly, wherein the battery pack is configured to be inserted distally into the battery port.

18. A surgical instrument comprising:
   (a) an end effector operable to treat tissue, wherein the end effector includes:
      (i) a first member, and
      (ii) a second member selectively actuatable relative to the first member to clamp tissue therebetween; and
   (b) a body assembly operatively coupled with the end effector, wherein the body assembly includes:
      (i) a battery pack, wherein the battery pack includes:
         (A) an outer wall,
         (B) a resilient arm extending along a portion of the outer wall, and
         (C) a plurality of first protrusions arranged along a length of the resilient arm, and
      (ii) a battery port configured to non-releasably receive the battery pack, wherein the battery port includes:
         (A) an inner wall, and
         (B) a plurality of second protrusions arranged along a length of the inner wall,
      wherein the first protrusions are configured to interlock with the second protrusions upon insertion of the battery back into the battery port and thereby inhibit subsequent removal of the battery pack from the battery port,
      wherein at least one of the second protrusions is configured to permanently deform in response to at least partial removal of the battery pack from the battery port and thereby render the surgical instrument inoperable.

19. The surgical instrument of claim 18, wherein the first protrusions are configured to ratchet along the second protrusions upon insertion of the battery pack into the battery port.

20. A surgical instrument comprising:
(a) an end effector operable to treat tissue, wherein the end effector includes:
   (i) a first member, and
   (ii) a second member selectively actuatable relative to the first member to clamp tissue therebetween; and
(b) a body assembly operatively coupled with the end effector, wherein the body assembly includes:
   (i) a battery pack, wherein the battery pack includes:
      (A) an outer wall,
      (B) a resilient arm extending along a portion of the outer wall, and
      (C) a plurality of catch elements arranged along a length of the resilient arm, and
   (ii) a battery port configured to non-releasably receive the battery pack, wherein the battery port includes:
      (A) an inner wall, and
      (B) a plurality of bosses arranged along a length of the inner wall,
   wherein the catch elements are configured to interlock with the bosses upon insertion of the battery back into the battery port and thereby inhibit subsequent removal of the battery pack from the battery port,
   wherein at least one of the bosses is configured to break away from the inner wall in response to an attempted removal of the battery pack from the battery port, thereby rendering the surgical instrument inoperable.

* * * * *